United States Patent [19]

Shibata et al.

[11] 4,075,062
[45] Feb. 21, 1978

[54] THROW-IN TYPE COLORIMETER

[75] Inventors: Takehiko Shibata, Wako; Tadahiko Ando, Tokyo; Tokuji Kitsunai, Asaka; Norio Kamiyama, Kawagoe; Yoshifumi Oikawa, Asaka, all of Japan

[73] Assignee: Rikagaku Kenkyusho, Japan

[21] Appl. No.: 693,758

[22] Filed: June 8, 1976

[30] Foreign Application Priority Data

June 11, 1975 Japan .................................. 50-70387

[51] Int. Cl.$^2$ ......................... C12K 1/00; G01N 21/26
[52] U.S. Cl. .............................. 195/103.5 R; 195/127; 356/208; 356/246
[58] Field of Search ........................ 195/103.5 R, 127; 356/208, 246

[56] References Cited

U.S. PATENT DOCUMENTS

| 2,896,502 | 7/1959 | Nordin | 356/208 |
| 3,490,850 | 1/1970 | Mayer | 356/246 |
| 3,560,099 | 2/1971 | Boe et al. | 356/246 |
| 3,819,278 | 6/1974 | Muller | 356/208 |
| 3,849,022 | 11/1974 | Hach | 356/208 |

Primary Examiner—Alvin E. Tanenholtz
Attorney, Agent, or Firm—Bucknam and Archer

[57] ABSTRACT

The present invention relates to a throw-in type colorimeter having a defoaming mechanism comprising a double-cylinder whereby it is possible to very easily detect the optical density of the solution to be examined, and more particularly to a thrown-in type colorimeter equipped with a defoaming device in which a downward flow is created in a cylinder by means of the liquid level column difference in the inlet of the cylinder to let the bubbles in the solution escape upwardly therefrom and also equipped with an upward solution flow passage to provide a communicating passage between the outer and inner cylinders to form a down flow in the outer cylinder and drive the remaining bubbles out of the solution in the outer cylinder by the twice reversed flow while removing the bubbles residing in the measuring chamber by the agitated solution flow.

6 Claims, 12 Drawing Figures

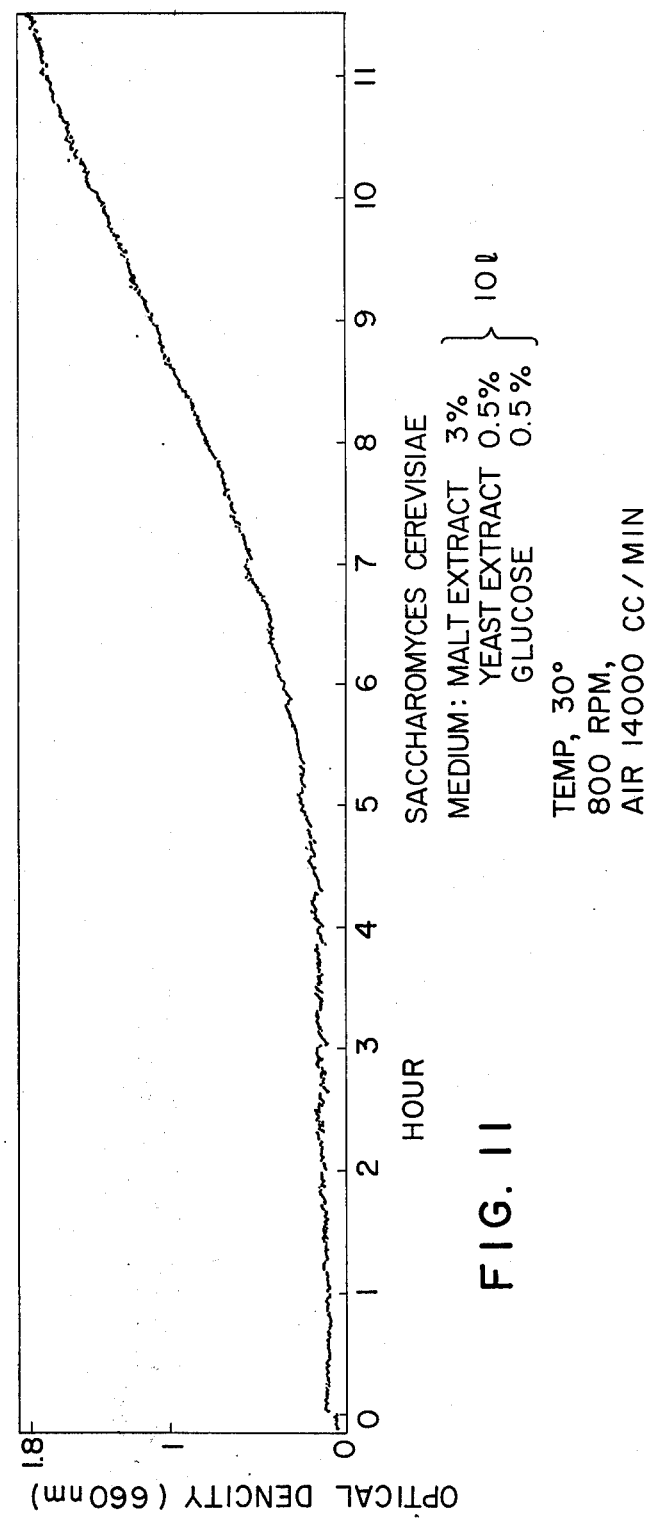

THROW-IN TYPE COLORIMETER

BACKGROUND OF THE INVENTION

1. Field of the Invention

Generally, in cultivation of the microorganisms, it is possible to know the cell density of microbes in the culture solution by measuring the optical density of the solution, so that it is of great consequence in the microbial industry to make accurate measurement of the optical density of the culture solution.

However, in culturing aerobic microorganisms, air bubbles are produced in great quantities in the agitation tank as air agitation is conducted therein, so that in measuring the optical density of a test solution by the colorimeter, said air bubbles often enter into the measuring chamber to excessively affect the light transmission rate owing to irregular reflection caused by such air bubbles, resulting in inaccurate measurement.

The present invention is to provide a colorimeter which permits accurate, easy and continuous measuring of the optical density of the solution to be examined by removing the air bubbles from the solution.

2. Description of the Prior Art

The basic mechanism of the colorimeter used in the present invention is preferably of the type which has been previously proposed by this inventor, but it is possible to use other types if they are capable of providing the same effects. The said previously proposed colorimeter is of the type in which the colorimeter is dropped into the solution to be checked so as to detect the optical density of the solution with ease from the photoelectromotive force indicated by a voltmeter connected to a photocell by a cable. Briefly, this type of colorimeter is constructed as follows. Light is projected from a light source through a color filter and a lens to a specimen chamber designed to allow free ingress and egress of the specimen (solution to be examined) so as to pass light from said light source through said specimen and to a photocell or phototransistor, said light source and photocell or phototransistor being respectively connected by a cable to a power source and a voltmeter which automatically records the absorbance.

SUMMARY OF THE INVENTION

The throw-in type colorimeter of this invention incorporates a defoaming device in combination with the above-said type of colorimeter and is also so designed to allow the solution to be examined to automatically circulate in said colorimeter by agitation of the culture solution.

Turbidity or absorbance of the culture solution can be determined by measuring the optical density of the solution, and as it is known that the optical density is proportional to the number of microbes in the culture solution, it is possible to know the number of microbes, that is to say, the cell density of microbes in the culture solution by measuring the optical density of the solution. In view of this, the present invention provides a throw-in type colorimeter equipped with a defoaming device by which the degree of growth of the microorganisms in the culture solution is determined by continuous measurement of the optical density of the solution by the colorimeter.

Generally, the optical density (OD) can be expressed by the following formula:

$$OD = \log (1 \text{ light transmission rate})$$

$$OD = -\log (\text{light transmission rate})$$

$$OD = -\log (\text{intensity of transmitted light intensity of incident light})$$

According to the throw-in type colorimeter of this invention, the device is dropped into the test solution so as to detect the density or turbidity with ease from the photoelectromotive force indicated by a voltmeter connected to the device by a cable. Therefore, when it is desired to know, for instance, the density of the culture solution during cultivation of microorganisms, one may simply drop this throw-in type colorimeter in the jar fermentor. It may also be directly dropped into a river, lake, water storage or such when it is desired to know the turbidity of water therein.

It is therefore an object of this invention to provide a throw-in type colorimeter which is remarkably effective in the measurement of the turbidity of water.

It is another object of this invention to provide a throw-in type colorimeter incorporating an automatic flow-down type defoaming device.

It is still another object of this invention to provide a defoaming throw-in type colorimeter which is capable of automatic and continuous recording of the optical density of the solution to be examined.

It is yet another object of this invention to provide a defoaming throw-in type colorimeter whereby it is possible to continuously measure the degree of growth of microorganisms in the fermenter from continuous measurement of the optical density of the aerobic culture solution.

Other objects of this invention will readily become apparent to those skilled in the art from the following detailed description of the invention.

BRIEF DESCRIPTION OF THE DRAWINGS

FIGS. 11 and 12 are graphs showing the results of measurement of optical density in cultivation of yeast (*Saccharomyces cerevisiae*) as obtained by use of the throw-in colorimeter of the present invention.

DETAILED DESCRIPTION OF THE PREFERRED EMBODIMENTS

The throw-in type colorimeter according to this invention has a double-cylinder structure in its upper portion, which is so designed as to create a downward flow of the test solution in the inner or outer cylinder by making use of the liquid level difference produced by rise of the liquid level formed on the outer side of the colorimeter as the solution is caused to flow against the colorimeter by the agitation of the solution, so as to allow the air bubbles in the solution to escape upwardly therefrom while the solution itself flows down in said cylinder, and then said solution flow is reversed in its flowing direction in an inner cylinder — outer cylinder communicating upward flow passage provided between said outer and inner cylinders so that the solution flows upwardly in the outer cylinder from the inner cylinder or in the inner cylinder from the outer cylinder, and upon reaching the end of said outer or inner cylinder, said solution flow is again reversed in its direction to flow now downwardly in the outer or inner cylinder. The air bubbles remaining in the solution are expelled upwardly by such double turn of the flow and the solution reaches an intermediate chamber to pass through a measuring chamber provided in the lower part of said intermediate chamber and is discharged downwardly from a bottom chamber provided at the bottom of said measuring chamber, and in this way, the test solution circulates in the colorimeter of this invention. Thus, the measuring chamber has a test solution inlet and outlet openings leading respectively into said intermediate chamber and bottom chamber so that the test solution may continuously flow into and out of the measuring chamber to allow continuous measurement of optical density of the solution. In the measuring chamber, light is projected from a light source at a lower position to the test solution in the measuring chamber through a color filter and a condensing lens, and the transmitted light is captured and measured in a photometric chamber provided with a photocells or a phototransistors disposed at a position opposing the light source. The light source and the photocell or phototransistor are connected respectively to a power source and a voltmeter by a cable so as to allow measurement of the optical density of the test solution.

Figure 1:
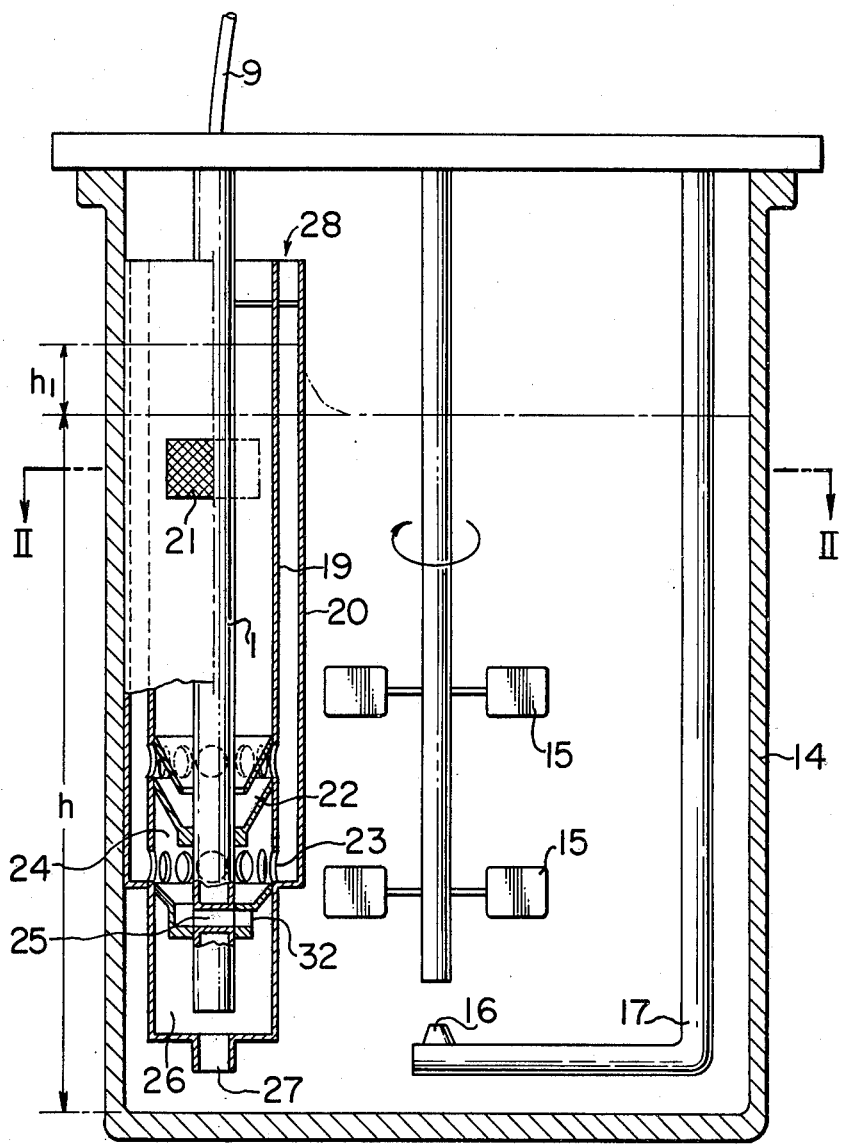
FIG. 1 is a schematic sectional view of a sulture tank or fermenter adapted with a throw-in type colorimeter having a defoaming device according to the present invention.
Figure 3:
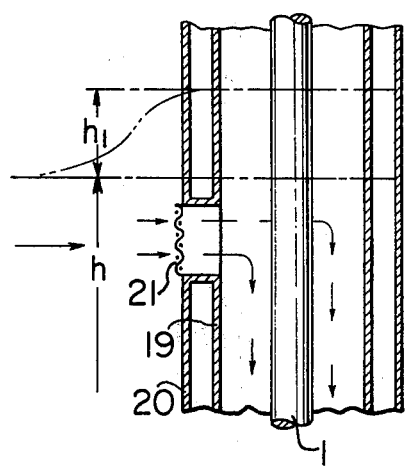
FIG. 3 is a sectional view taken along the line III—III of FIG. 2, showing on an enlarged scale a culture solution inlet to the inner cylinder of the colorimeter of this invention.

Now, the colorimeter of this invention is described in detail by way of an embodiment where the colorimeter is installed in a culture tank. In the explanation of this embodiment, the culture solution is assumed to flow first into the inner cylinder from the inlet thereof, but the following description of course also applies to the case where the culture solution first flows into the outer cylinder and then into the inner cylinder. In FIG. 1, it will be seen that an agitator 15 is provided in an agitation tank 14, said agitator 15 being turned to agitate the culture solution while sterilized air is injected from a nozzle supplied through an air pipe 16 so as to perform cultivation under agitation. With no agitation, the liquid level in the tank 14 is as seen in FIG. 3 equal to the liquid level ($h$) in the outer cylinder 20 and inner cylinder 19 of the defoaming device.

Figure 2:
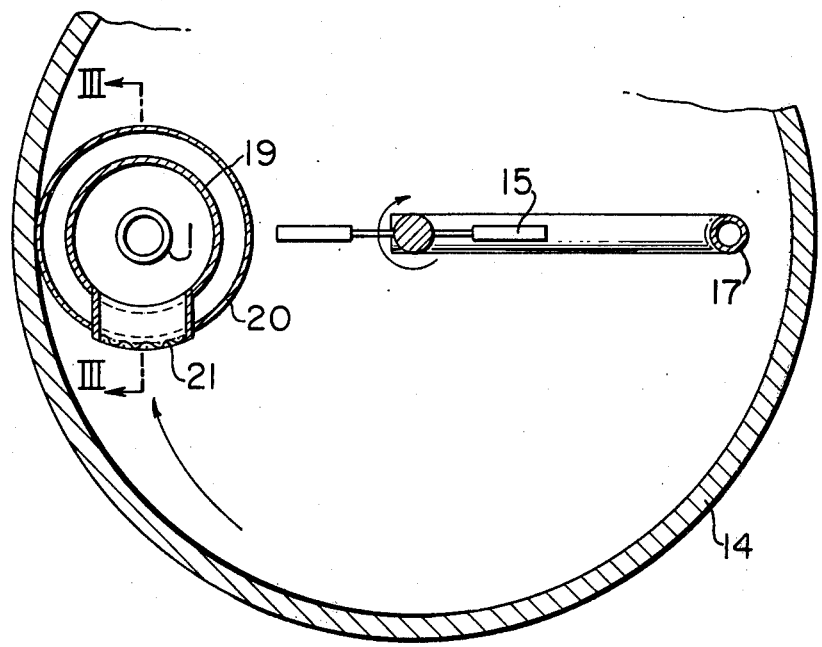
FIG. 2 is a sectional view taken along the line II—II of FIG. 1.

When agitation is started, the culture solution is urged to flow in the direction of the arrows in FIG. 2, and when the solution hits the outer cylinder 20 it rises up along said outer cylinder by the height of $h_1$. Therefore, the culture solution which has flown into the inner cylinder 19 from the inlet 21 provided in opposition to the direction of agitation of the culture solution is substantially equalized in its level with the solution which has risen up along the outer cylinder 20 and becomes higher by $h_1$ than the surrounding liquid level $h$. Thus, the culture solution flows into the inner cylinder 19 while being cleared of the air bubbles having a size greater than the mesh of the screen provided at the inlet 21 of the outer cylinder 20. Further, the bubbles still remaining in the solution are removed upwardly while the solution flows down slowly in the inner cylinder 19.

In the apparatus of this invention, it is desirable to obtain a suitable liquid level difference $h_1$. For example, in case of using a culture tank with a diameter of 20 cm, it is possible to obtain the desired liquid level difference $h_1$ by using an agitation velocity higher than 150 r.p.m. As apparent to those skilled in the art, the above-described principle can be applied to the case where the test solution first flows into the outer cylinder and then it is guided into the inner cylinder and thence into the intermediate chamber, The downward flow in the inner cylinder 19 is reversed in its direction upon reaching the inner cylinder — outer cylinder connecting upward flow passage provided at the lower end of the inner cylinder. Thus, the solution flows upwardly in said passage, and upon reaching its end, the solution flow is again reversed in its direction to flow now downwardly in the outer cylinder 20. By these two reversals of the flow direction, the air bubbles contained in the solution flow are perfectly driven out of the solution and, rising in the outer cylinder 20 are discharged. Then the thus obtained air bubble free culture solution flows into the inner cylinder from the outer cylinder and thence into the intermediate chamber 24 through the inlets 23 to pass through the measuring chamber 25 provided at the lower part of said intermediate passage for measurement of the optical density of the solution. It then flows into the bottom chamber 26 from a discharge port 32 of the measuring chamber and thence is discharged out from a discharge port 27 circulate in the culture tank. The time of residence of the specimen in the present colorimeter is approximately 1 to 3 minutes, and deviation in the measurement can be ignored.

Said intermediate chamber and bottom chamber are provided for the purpose of ensuring smooth and correct measuring operation by obtaining stable solution flow in the measuring chamber through interference of the solution flow from the outer cylinder as well as the solution flow in the measuring chamber caused by agitation in the culture tank, so that such chambers can be embodied in a variety of configurations such chambers may be vacant spaces in a most simple example, or, if desired, a baffle plate may be provided in each such space. Usually, the vacant spaces such as shown in the drawings suffice for the purpose. The same object can, in some case, be accomplished without providing one or even both of such chambers. It will be also obvious that the shape of the upward flow passage connecting the inner and outer cylinders may be selected suitably according to the purpose of use.

Thus, according to the colorimeter of this invention, it is possible to easily and continuously measure the optical density of the culture solution without requiring the attendance of a worker and it is also possible to automatically record the measurements by connecting the colorimeter of this invention to a recorder by a cable. Further, the output of this device can be utilized for various types of automatic controls.

Figure 4:
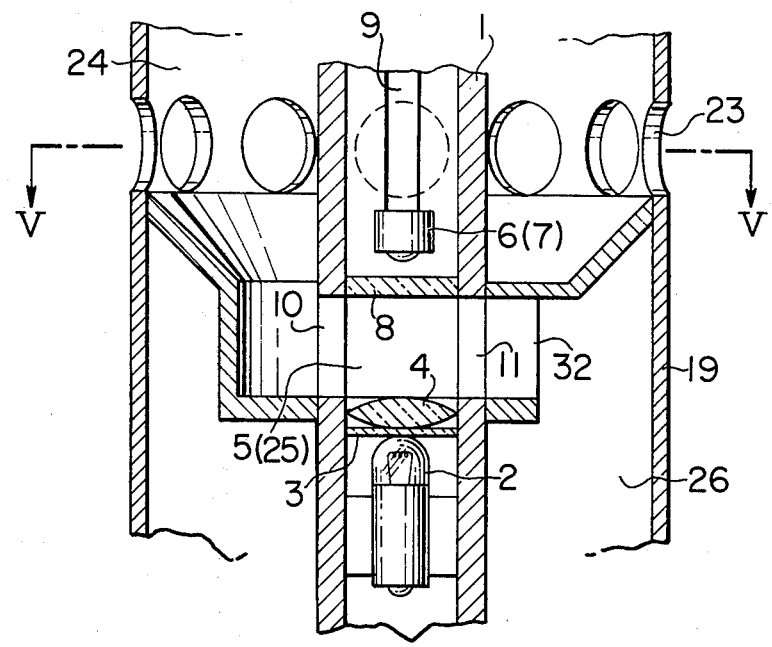
FIGS. 4 and 5 are schematic englarged drawings of the intermediate passage and specimen chamber, respectively.
Figure 5:
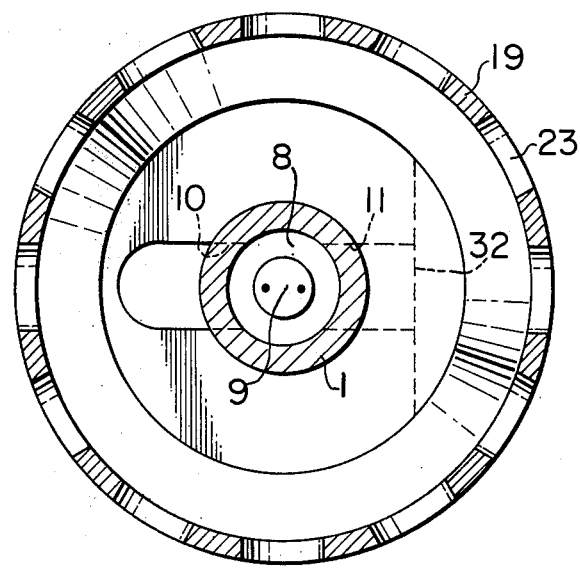

Now, the mechanism of the colorimeter portion of the throw-in type colorimeter installation of this invention is described with particular reference to FIGS. 4 and 5. This colorimeter is of a cylindrical structure with diameter of 10 to 50 mm and contains in the light source chamber a light source 2, a color filter 3, a lens 4, a specimen measuring chamber 5, and contains in light measuring chamber a photocell 6 or a phototransistor 7 and a window 8, said photocell or phototransistor being connected to an outside constant-voltage power supply and a DC voltmeter, respectively, by a cable 9.

In operation, the colorimeter 1 is installed in an agitated solution to be tested, whereby the solution flows into the colorimeter from the upper inlet and hence flows into the measuring chamber 5 and after passing said chamber 5, it flows out from an outlet 11. Thus, the light emitted from the light source 2 through the color filter 3 and lens 4 passes through the specimen and is projected onto the photocell 6 or phototransistor 7 through the window 8, and the optical density of the specimen can be known from the indication of photoelectromotive force given by the DC voltmeter connected to said photocells or phototransistors by a cable 9. The light source 2 used in this invention may be of any type if it can provide light of a wave length within a certain range. The photocell 6 or phototransistor 7 used for measurement of transmitted light may be optionally selected according to the purpose of use. Also, the length of the cable 9 may be suitably selected depending on the depth of the test solution.

Figure 6:
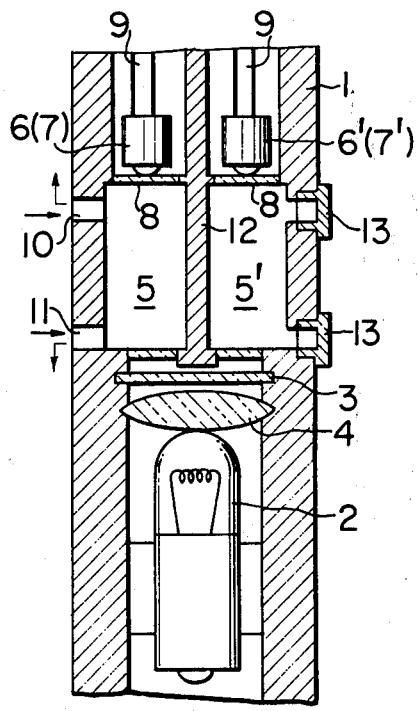
FIG. 6 is a side view, with parts shown in section, of an embodiment of the present apparatus in which two photocells or phototransistors as well as a specimen measuring chamber and a control sample measureing chamber are provided.

Referring now to FIG. 6, there is shown in side elevation, with parts in section, an embodiment where two photocells or phototransistors as well as a specimen measuring chamber and a control sample measuring chamber are provided. It will be seen that said specimen measuring chamber 5 and control sample measuring chamber 5' as well as two photocells 6, 6' or phototransistors 7, 7' are provided in the respective compartments formed in the cylinder 1 by a partition plate 12, and they are arranged such that light from the light source 2 will be projected uniformly thereto through a color filter 3 and a lens 4.

Numeral 13 designates plugs which serve both as sample inlet and outlet for the control sample measuring chamber 5'. In case no sufficiently stable constant-voltage power supply is obtainable, a control sample such as for example a solvent or water is introduced into this control sample measuring chamber 5' by opening said plugs 13, which are closed after filling. By freely introducing the specimen material into the specimen measuring chamber 5, it is possible to detect the optional density of the specimen by the voltmeter from the voltage ratio between the two chambers. The specimen measuring chamber 5 is provided with openings 10, 11 for introducing and discharging the specimen.

Thus, since the photocells 6, 6' or phototransistors 7, 7' are connected to the voltmeter by cable 9, the optical density of the specimen can easily be detected by the voltmeter from the voltage ratio between the specimen measuring chamber side and the control sample measuring chamber side.

Although the structure of the measuring chamber in a preferred embodiment has been described, it is possible to employ many other types of structure, and continuous measurement can be performed by continuously passing the test solution between the light source and the photometric chamber. It is particularly desirable to employ a structure which makes it possible to minimize the portion where the flow solution is likely to stagnate, so as to prevent accumulation or deposition of microbes.

While the throw-in type colorimeter of this invention has been described with reference to the accompanying drawings by way of a mere embodiment thereof, it will be apparent to those skilled in the art that various changes or modifications can be made with ease on the basis of the foregoing description without departing from the spirit of this invention, and all of such changes and modifications are involved within the scope of this invention.

TEST EXAMPLE 1

In this example there is described a case wherein as one of the typical microorganisms used in microbial industry *Bacillus substilis* was cultured in a culture tank equipped with a throw-in type colorimeter with a defoaming device of this invention and the optical density of the cultured microbes was measured.

Figure 7:
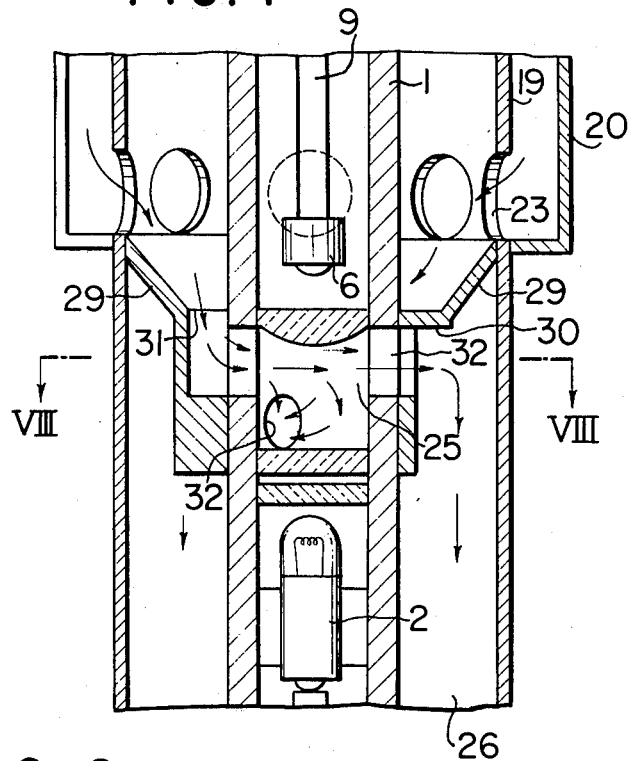
FIGS. 7 and 8 are schematic enlarged views of the intermediate passage and measuring chamber used in the present apparatus.
Figure 8:
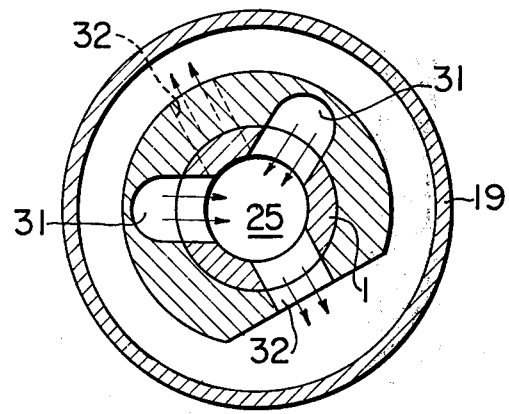

The apparatus used in this example has an intermediate passage and a measuring chamber such as shown in FIGS. 7 and 8. The culture solution is flown into the colorimeter from inlet 21, flowed down inner pipe 19 passed through inner and outer tube connecting passage, flowed down outer tube and introduced into the intermediate passage 24 from a plurality of inlet openings 23 is throttled in its flow by a conical side wall 29 and further flows down into the measuring chamber 25 from an opening 31 provided in a partition wall 30 of the intermediate passage 24. In the measuring chamber 25, light from a light source (a lamp having a lens at its end) is projected through a condensing lens to measure the optical density by a phototransistor 7. After measurement, the test solution enters the bottom chamber from openings 32, 32'. During this time, the air bubbles adhering to the underside of the window at the top of the measuring chamber are washed away by the flow of the solution entering from the opening 31.

The throw-in type colorimeter with defoaming device used in this example is 40 cm in total length and 60 mm in outer diameter and has a 10 mm$\phi$ × 10 mm measuring chamber having a 15 mm square inlet opening. This colorimeter was dropped into a constant-temperature air agitation type microorganism fermenter (Microferm Fermenter MF-114 mfd. by New Branswich Inc. in U.S.A. and measuring 22 cm in inner diameter, 45 cm in height and 14 liter in capacity), and cultivation of microorganisms was carried out under aeration and agitation by using this fermenter and the cell density of the microorganisms in the course of cultivation was automatically recorded by a recorder from continuous measurement of the optical density.

Figure 9:
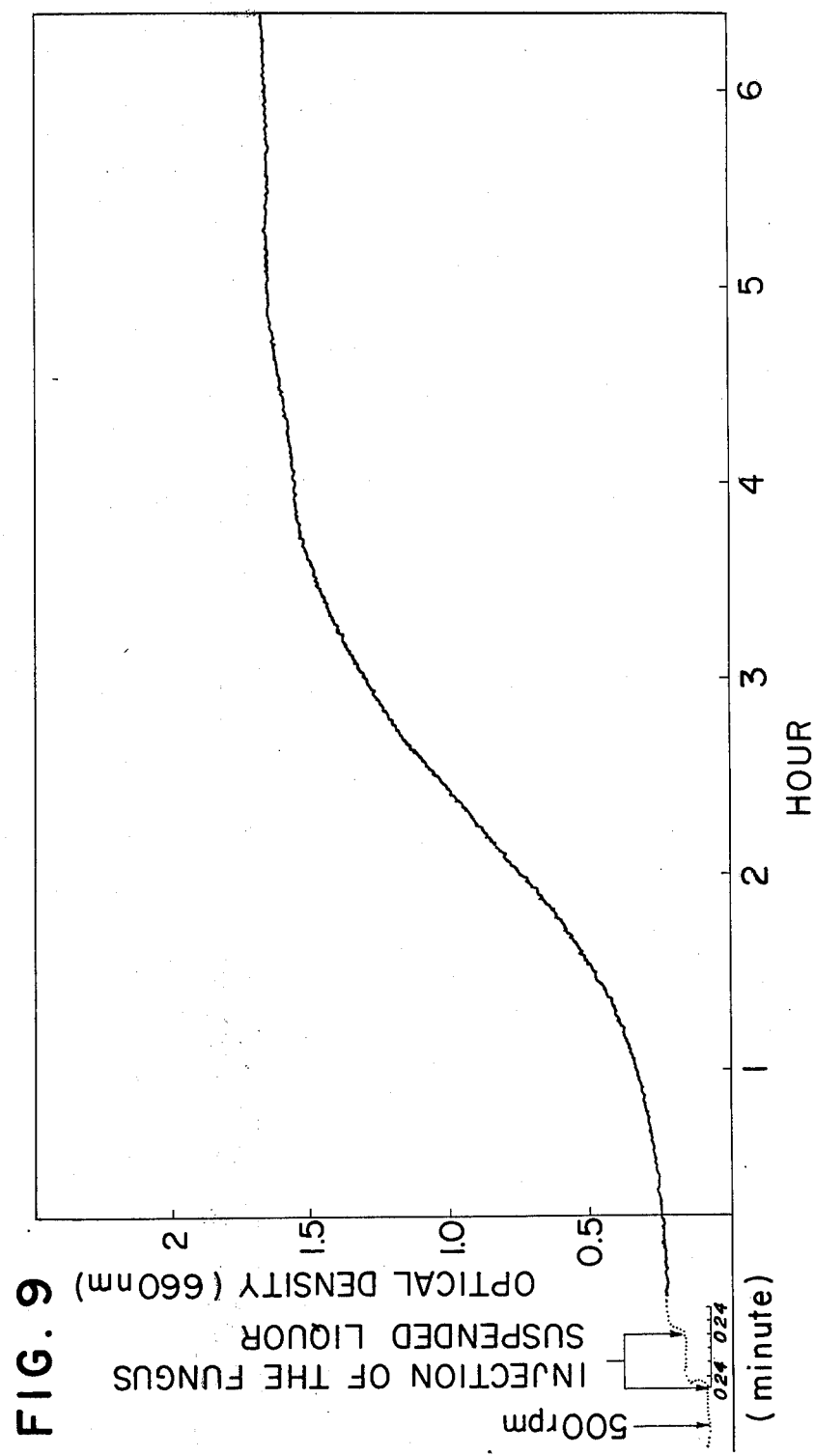
FIGS. 9 and 10 are graphs showing the results of measurement of optical density in cultivation of *Bacillus subtilis* by use of the throw-in type colorimeter of the present invention.

First, 10 liter of culture medium (containing 100 gr of polypeptone, 25 gr of yeast extract and 25 gr of sodium chloride and adjusted to pH 7.0) was placed in said fermenter and then it was subjected to 30-minute high-pressure steam sterilization under 1 kg/cm$^2$ and, after cooling, was maintained at 37° C. Then there was added thereto 200 ml of a pre-culture solution prepared from 20-hour shaking culture of *Bacillus subtilis* Marburg GSY 1026 strain on said TB culture medium at 37° C, and after approximately eight-minute air agitation, 200 ml of the same pre-culture solution was further added, followed by cultivation at 37° C, aeration rate of 6,000 ml/min and agitation of 500 turns/min. The liquid level difference observed in this operation was approximately 10 mm. The optical density measured by light of 660 nm wave length, which indicates the cell density of microbes in the course of cultivation, increased as a function of time as shown in the graph of FIG. 9.

Figure 10:
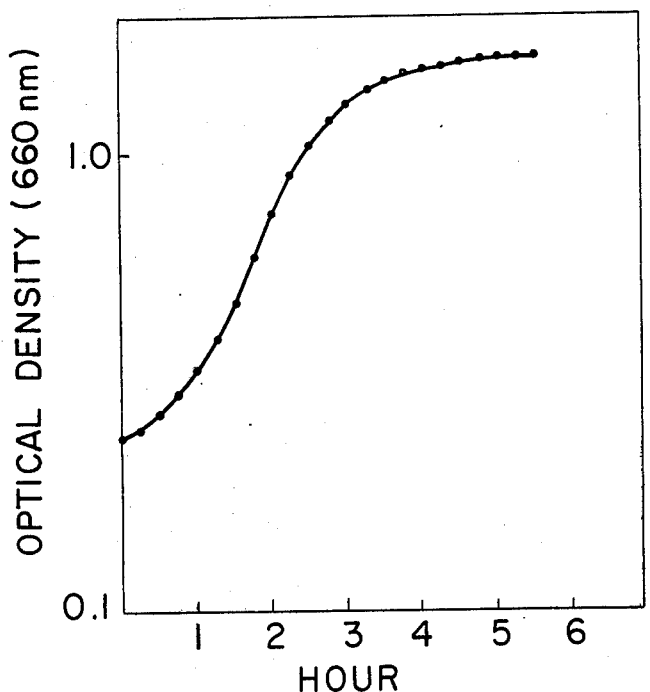

Plotting of this turbidity curve by way of a logarithmic scale provided a growth curve such as shown in the graph of FIG. 10. These results of measurement indicate that the measurements were accomplished without any influence of the air bubbles in the apparatus of this invention. In case of adding a microbe suspension, the added microbes were dispersed in the tank in two minutes after addition and the corresponding optical density was obtained as shown at the left end of the graph of FIG. 9, this being indicative of almost no delay in measurement.

As described above, the cell density in the fermenter could be very clearly measured by use of the apparatus of the present invention.

TEST EXAMPLE 2

Figure 12:
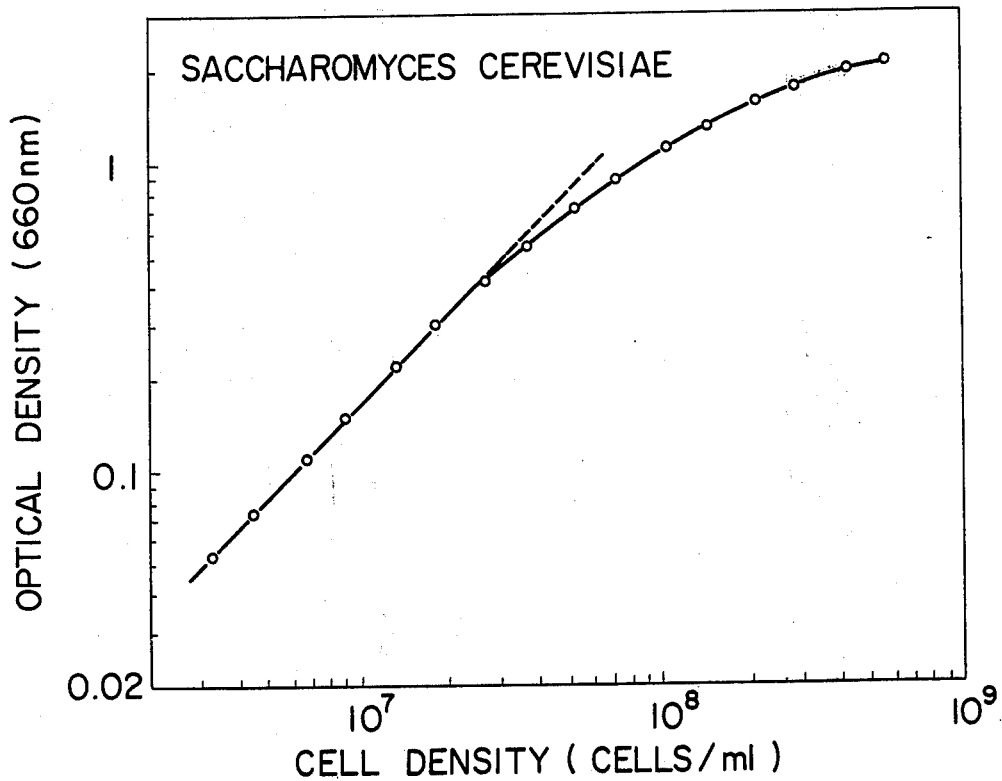

The process of Example 1 was repeated for culturing *Saccharomyces cerevisiae*, a kind of yeast, by using a culture medium containing 3% malt extract, 0.5% yeast extract and 0.5% glucose at 30° C under agitation of 800 rpm and aeration rate of 14,000 cc/min, obtaining the results shown in FIGS. 11 and 12. FIG. 12 is a logarithmic graphic representation of the results shown in FIG. 11.

What we claim is:

1. A throw-in type colorimeter comprising: (a) a two-cylinder structure consisting of an inner cylinder and an outer cylinder, both opened at the upper end, and also having a test solution inlet which opens only into one of said cylinders; (b) first means for reversing the direction of the flowing solution which flows into said inlet and flows downwardly into said one of said cylinders, said first means being provided at the lower end of said two-cylinder structure and connecting said cylinder having said inlet to the other cylinder; (c) second means for again reversing the flowing direction of the upwardly flowing solution, which was obtained by said first means, so that the test solution flows downwardly through said other cylinder; (d) an intermediate chamber for regulating the solution flow, said intermediate chamber being provided at the lower end of said two-cylinder structure and having a solution inlet which communicates with said second means; (e) a measuring chamber, conduit means between the bottom of said measuring chamber and said intermediate chamber; (f) a test solution discharge port, means for communicating said measuring chamber and said test solution discharge port; (g) means for measuring the light transmission rate of the solution which passes through said measuring chamber located in said measuring chamber and (h) a photometric chamber for measuring the light transmission rate of the test solution flowing circulatively from said inlet to said discharge port owing to the liquid level difference created by impingement of the flowing solution against the external surface of the outer cylinder.

2. A throw-in type colorimeter according to claim 1, wherein a light source chamber and a photometric chamber are provided on both sides of the measuring chamber, and light from said light source chamber is captured in said photometric chamber to measure the optical density of the test solution in said measuring chamber.

3. A throw-in type colorimeter according to claim 1, wherein a bottom chamber is provided at the bottom of the measuring chamber so as to prevent disturbance of the test solution in the measuring chamber caused by flowing motion of the solution to be measured.

4. A method of cultivation in which a thrown-in type colorimeter is provided in an aerobic fermentation culture tank and the optical density of the culture solution is measured in a measuring chamber so as to carry out cultivation while constantly observing the degree of growth of the microbes in said tank, which comprises the steps of introducing said culture solution into a defoaming device located in said culture tank, said defoaming device comprising a two-cylinder structure consisting of an inner cylinder and an outer cylinder, both opened at the top, said structure having a solution inlet opening into the inner cylinder and positioned in opposition to the solution flow in said culture tank, allowing the culture solution to flow into the inner cylinder by virtue of the liquid level difference obtained from the rise of the liquid level caused by impingement of the solution flow in the tank against the colorimeter, letting the air bubbles contained in the culture solution escape upwardly from the solution which in turn flows down in the inner cylinder, then reversing said downward solution flow in its direction by a first flow reversing passage provided at the lower end of said two-cylinder structure whereby the solution flows upwardly and then again reversing the direction of flow by a second flow reversing passage whereby the solution flows downwardly to thereby drive the fine air bubbles out of the culture solution flowing in the outer cylinder, with the resultant bubble-free culture solution being then caused to flow down in the outer cylinder and then guiding the culture solution into the measuring chamber where absorbance of the culture solution is measured continuously while discharging the measured solution into the tank, thereby to allow continuous determination of the optical density of the test solution.

5. A cultivation method according to claim 4, wherein an intermediate chamber is provided at the lower end of the outer cylinder to guide the downward flow in the outer cylinder into the measuring chamber through said intermediate chamber so as to obtain a gentle flow of the solution in said measuring chamber to allow stable measuring of the solution.

6. A cultivation method according to claim 4, wherein a bottom chamber is provided at the bottom of the measuring chamber so as to stabilize the solution flow in said measuring chamber by keeping it free of influence of the flow in the tank to thereby allow stable measurement of the solution.

* * * * *